(12) United States Patent
Hashimoto et al.

(10) Patent No.: US 7,069,791 B2
(45) Date of Patent: Jul. 4, 2006

(54) ARRAY-TYPE CAPACITIVE PRESSURE PULSE WAVE SENSOR, AND PULSE WAVE MEASURING APPARATUS HAVING THE SAME

(75) Inventors: Masao Hashimoto, Kyoto (JP); Kazuhisa Tanabe, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/175,447

(22) Filed: Jul. 7, 2005

(65) Prior Publication Data

US 2006/0005631 A1   Jan. 12, 2006

(30) Foreign Application Priority Data

Jul. 8, 2004   (JP)   ............................. 2004-210359

(51) Int. Cl.
*G01B 7/16*   (2006.01)
(52) U.S. Cl. ...................................... 73/780
(58) Field of Classification Search .................... 73/780
See application file for complete search history.

(56) References Cited

U.S. PATENT DOCUMENTS 4,269,193 A   5/1981   Eckerle ...................... 128/672

FOREIGN PATENT DOCUMENTS

JP   63-293424   11/1988

OTHER PUBLICATIONS

G. L. Pressman, P. M. Newgard, "A Transducer for the Continuous External Measurement of Arterial Blood Pressure", IEEE Transactions on Bio-Medical Electronics, 1963, pp. 73-81.
R. S. Fearing, "Tactile Sensing Mechanisms", The International Journal of Robotics Research, Jun. 1990, vol. 9, No. 3, pp. 3-23.
D. A. Kontarinis et al., "A Tactile Shape Sensing and Display System for Teleoperated Manipulation", IEEE International Conference on Robotics and Automation, 1995, pp. 641-646.

*Primary Examiner*—Max Noori
(74) *Attorney, Agent, or Firm*—Morrison & Foerster LLP

(57) ABSTRACT

An array-type capacitive pressure pulse wave sensor includes m rows of lower electrodes arranged in parallel with each other to extend substantially linearly in a direction approximately orthogonal to the extending direction of the artery at the time of measurement, n columns of upper electrodes arranged in parallel with each other at a prescribed distance from the m lower electrodes to extend in a direction crossing the extending direction of the m lower electrodes, and m×n capacitive elements formed at intersections of the m lower electrodes and the n upper electrodes. The m×n capacitive elements are arranged in a staggered manner when the pressure detecting portion is seen in two dimensions. Thus, it is possible to provide an array-type capacitive pressure pulse wave sensor that can be manufactured inexpensively and that ensures accurate and stable measurement of the pressure pulse wave.

3 Claims, 17 Drawing Sheets

ARRAY-TYPE CAPACITIVE PRESSURE PULSE WAVE SENSOR, AND PULSE WAVE MEASURING APPARATUS HAVING THE SAME

BACKGROUND OF THE INVENTION

1. Field of the Invention

The present invention relates to an array-type capacitive pressure pulse wave sensor for measuring a waveform indicating a change in arterial pressure, and a pulse wave measuring apparatus provided with the same.

2. Description of the Background Art

As a pressure pulse wave measuring method for obtaining a waveform indicating a change in arterial pressure in a noninvasive and simple manner, a tonometry method is known, which is described in G. L. Pressman, P. M. Newgard, "A Transducer for the Continuous External Measurement of Arterial Blood Pressure", IEEE TRANSACTIONS ON BIO-MEDICAL ELECTRONICS, 1963, pp. 73–81 (hereinafter, referred to as "Publication 1"). According to the tonometry method, a flat plate is pressed against the surface of the living body to deform the underlying artery to a flattened form, and, with the surface of the artery being kept in the state where the influence of the tension is eliminated, only the change in arterial pressure is measured accurately and stably.

In recent years, attempts have been made to measure the states within the living body by obtaining characteristic values from the waveform indicating the change in arterial pressure measured by using the tonometry method. As one of such attempts, investigation of the AI (Augmentation Index) value as an index for determination of degree of hardening of the artery has been conducted vigorously.

Measurement of the waveform indicating the change in arterial pressure using the tonometry method requires, not only that the artery is flattened, but also that a sensor element is arranged directly above the flattened artery. Further, to conduct the measurement of the waveform indicating the change in arterial pressure with accuracy, it is necessary to ensure that the sensor element has a width smaller than the width of the flattened part of the artery. To this end, the sensor element needs to be sufficiently small compared to the diameter of the underlying artery. In view of the foregoing, since it is very difficult to position a single sensor element immediately above the flattened region of the artery, it is practical to use a pressure sensor having a plurality of microfabricated sensor elements arranged approximately orthogonal to the direction in which the artery extends, to measure the pressure pulse wave.

U.S. Pat. No. 4,269,193 (hereinafter, referred to as "Publication 2") and Japanese Patent Laying-Open No. 63-293424 (hereinafter, "Publication 3") disclose the pulse wave measuring apparatuses implementing the measurement principle described above. In each of the pressure pulse wave sensors disclosed in Publications 2 and 3, the sensor element has a width (of about 0.2 mm to 0.5 mm) that is sufficiently smaller than the diameter of the artery (normally on the order of 1.2 mm to 3.5 mm), and a large number of such miniaturized sensor elements are arranged in the direction approximately orthogonal to the extending direction of the artery, so that at least one sensor element is positioned directly above the flattened artery.

In the pulse wave measuring apparatus disclosed in Publication 2, as a pressure sensor satisfying sensitivity and S/N ratio of required levels, a semiconductor pressure sensor having a plurality of diaphragms formed in a monocrystalline silicon chip by anisotropic etching is described. Further, in the pulse wave measuring apparatus disclosed in Publication 3, use of a piezoelectric element, a semiconductor strain gage, or a pressure-sensitive diode or transistor formed on a semiconductor chip, as a pressure sensor is described. Pressure sensors utilizing such strain resistance elements are suitable for the pressure sensor satisfying the above-described conditions, since they can be miniaturized by applying a semiconductor manufacturing process or the like. Such miniaturization of the sensor element, however, inevitably increases the manufacturing cost to a large extent.

Generally, as the sensing technique for measuring pressure, the one utilizing a capacitive element is known, besides the one utilizing the strain resistance element. In the sensing technique utilizing the capacitive element, the sensor element has a relatively simple structure compared to that of the strain resistance element, which can be manufactured inexpensively without the need of using the semiconductor manufacturing process requiring a large manufacturing cost.

Although not intended to be used for obtaining a waveform indicating a change in arterial pressure, as a pressure sensor having capacitive elements arranged in an array on a sensing surface, tactile sensors are described in R. S. Fearing, "Tactile Sensing Mechanisms", The International Journal of Robotics Research, June 1990, Vol. 9, No. 3, pp. 3–23 (hereinafter, "Publication 4") and in D. A. Kontarinis et al., "A Tactile Shape Sensing and Display System for Teleoperated Manipulation", IEEE International Conference on Robotics and Automation, 1995, pp. 641–646 (hereinafter, "Publication 5").

Hereinafter, of the tactile sensors described in Publications 4 and 5, the one described in Publication 5 will be described in detail. FIG. 16 is a perspective view of a pressure detecting portion of a tactile sensor described in Publication 5, and FIG. 17 is an exploded perspective view of the pressure detecting portion shown in FIG. 16. FIG. 18A is a plan view of the pressure detecting portion of FIG. 16 when seen from the above, and FIG. 18B is a schematic diagram showing a layout of the capacitive elements in the pressure detecting portion of FIG. 16. FIG. 19 is a circuit configuration diagram of the tactile sensor including the pressure detecting portion shown in FIG. 16.

As shown in FIGS. 16 and 17, the tactile sensor 1E described in Publication 5 primarily includes lower electrodes 10, upper electrodes 20, and spacer members 30. Lower electrodes 10 are formed of a plurality of copper strips that are arranged side by side in rows to extend substantially linearly. Upper electrodes 20 are formed of a plurality of copper strips that are arranged side by side in columns to extend substantially linearly in a direction orthogonal to lower electrodes 10. Spacer members 30 formed of silicon rubber are arranged between lower electrodes 10 and upper electrodes 20.

At each of the intersections of lower electrodes 10 and upper electrodes 20 arranged in rows and columns, a part of lower electrode 10 and a part of upper electrode 20 face each other with a prescribed distance therebetween secured by spacer members 30. In this manner, capacitive elements 40 (see FIG. 18A) serving as the sensor elements are formed at the intersections.

As shown in FIGS. 18A and 18B, in tactile sensor 1E of the above-described configuration, capacitive elements 40 are aligned in the form of an array when the pressure detecting portion is seen in two dimensions. Each capacitive element 40 has its capacitance changed as pressure applied to upper electrode 20 or lower electrode 10 causes them to deflect in the direction decreasing the distance therebetween.

Now, with lower electrodes 10 and upper electrodes 20 arranged in rows and columns, assume a circuit configuration where one electrodes, i.e., the lower electrodes or the upper electrodes, are connected via a multiplexer 50 to a power source 60 and the other electrodes, i.e., the upper electrodes or the lower electrodes, are connected via multiplexer 50 to a detector 70, as shown in FIG. 19. With this configuration, when a particular lower electrode 10 and a particular upper electrode 20 are selected by means of multiplexer 50, capacitance of a specific one of the capacitive elements 40 arranged in the array form can be obtained via detector 70. For example, in FIG. 19, when lower electrode 10 on the second row from the top and upper electrode 20 on the third column from the left are selected, the capacitance of the capacitive element denoted by a reference character 41 is output. Thus, it is possible to measure the pressure at a given position on the sensing surface of tactile sensor 1E.

If the conventional pressure sensor of capacitive type as described above is used as the pressure pulse wave sensor for measuring the pressure pulse wave, the manufacturing cost will be considerably decreased compared to the case of the pressure sensor using the strain resistance elements described above. However, the capacitive type pressure sensor is inferior in terms of miniaturization compared to the pressure sensor using the strain resistance elements manufactured by the semiconductor process. The currently workable minimum width of the capacitive element is about 1.0 mm to 2.0 mm.

When the capacitive pressure sensor of the above-described structure is used as the pressure pulse wave sensor, misalignment between the central position of the sensor element and the central position of the artery will be A/2 at a maximum when the distance between the neighboring sensor elements is represented by A, as shown in FIG. 18B. Thus, the maximum amount of misalignment between the central position of the sensor element and the central position of the artery when the capacitive pressure sensor of the above structure manufactured with the currently workable minimum width dimension is used as the pressure pulse wave sensor will be about 0.5 mm to 1.0 mm. This is considerably inferior to the case where the pressure sensor of strain resistance type described above is used as the pressure pulse wave sensor. If such a capacitive pressure sensor is adapted as it is, there will occur a large error in the measured value, hindering measurement with high accuracy.

SUMMARY OF THE INVENTION

An object of the present invention is to provide an array-type capacitive pressure pulse wave sensor that can be manufactured inexpensively and that can measure the pressure pulse wave accurately and stably, and a pulse wave measuring apparatus incorporating the same.

An array-type capacitive pressure pulse wave sensor according to the present invention is for measuring a waveform indicating a change in arterial pressure by pressing a surface of a living body, and includes: m rows (m is a natural number of more than 1) of first electrodes arranged in parallel with each other to extend substantially linearly in a direction approximately orthogonal to an extending direction of an artery at the time of measurement; n columns (n is a natural number of more than 1) of second electrodes arranged in parallel with each other at a prescribed distance from the m first electrodes to extend in a direction crossing the extending direction of the m first electrodes; and m×n capacitive elements formed at intersections of the m first electrodes and the n second electrodes, wherein the m×n capacitive elements are arranged in a staggered manner when seen in two dimensions.

With this configuration, it is possible to increase the arrangement density of the capacitive elements in the direction approximately orthogonal to the extending direction of the artery. Accordingly, accurate and stable measurement of pressure pulse wave is ensured even when the pressure sensor of capacitive type that can be manufactured inexpensively is used as the pressure pulse wave sensor.

In the array-type capacitive pressure pulse wave sensor according to the present invention, each of the n second electrodes preferably has a bent portion that is provided at a part of the second electrode located between the neighboring two first electrodes and not overlapping either of the relevant first electrodes. The bent portion is bent in a direction crossing the extending direction of the artery.

With this configuration, it is possible to readily produce an array-type capacitive pressure pulse wave sensor having capacitive elements arranged in a staggered manner.

Alternatively, in the array-type capacitive pressure pulse wave sensor according to the present invention, the n columns of second electrodes may extend substantially linearly, and the m rows of first electrodes and the n columns of second electrodes cross each other not orthogonally when seen in two dimensions.

With this configuration, the array-type capacitive pressure pulse wave sensor having capacitive elements arranged in a staggered manner can readily be produced.

A pulse wave measuring apparatus according to the present invention includes: a sensor unit having any of the array-type capacitive pressure pulse wave sensors described above; a securing member for securing the sensor unit with respect to the living body; and a pressing member for pressing the array-type capacitive pressure pulse wave sensor against the living body.

With this configuration, it is possible to produce inexpensively a pulse wave measuring apparatus capable of measuring the pressure pulse wave accurately and stably.

According to the present invention, highly accurate measurement of the pressure pulse wave using a pressure sensor of capacitive type that can be produced inexpensively becomes possible.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
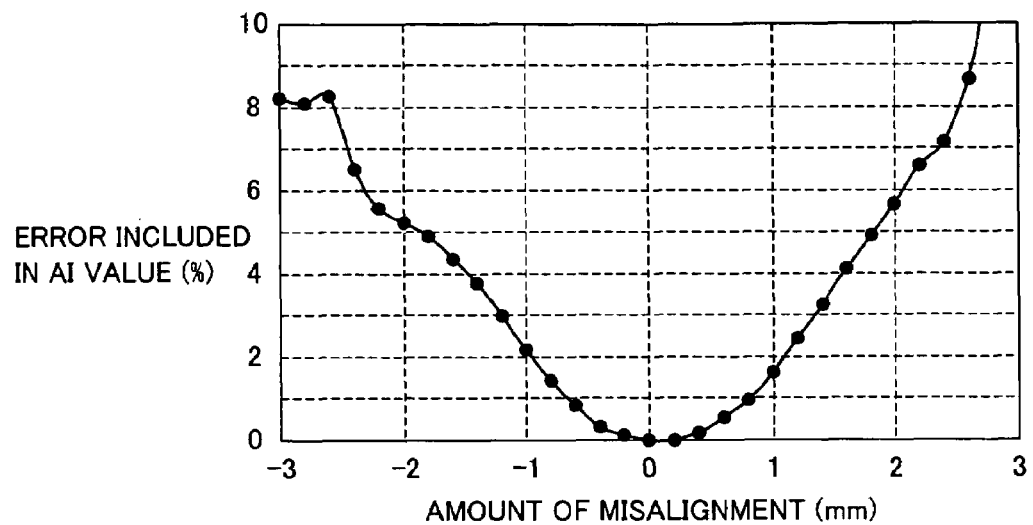
FIG. 1 is a graph showing a result of testing as to what degree of error will be included in the AI value when the central position of the sensor element is misaligned with the central position of the artery.

When a pressure sensor of capacitive type manufactured with the currently workable minimum width dimension is used as a pressures pulse wave sensor, there occurs misalignment of about 0.5 mm to 1.0 mm between the central position of the sensor element and the central position of the artery. The inventors carried out testing to verify to what extent such misalignment would affect the accuracy in measurement of the AI value. FIG. 1 is a graph showing a result of the testing as to what degree of error will be included in the AI value when the central position of the sensor element is misaligned with the central position of the artery at the time of measurement. As shown in FIG. 1, as the misalignment of the central position of the sensor element with the central position of the artery increases, the error included in the AI value increases accordingly. It was found from the result of the testing that the AI value includes an error of about 0.5% when the misalignment is 0.5 mm, and the AI value includes an error of about 2% with the misalignment of 1.0 mm. This means that the result of measurement of the AI value will include an error of about 0.5% to 2% at a maximum even when the capacitive pressure sensor manufactured with the currently workable minimum width dimension is used as the pressure pulse wave sensor. It was thus confirmed that accurate measurement of pressure pulse wave would not be possible if such a sensor is brought to practical use without modification.

Under these circumstances, the inventors vigorously conducted investigation to see whether improving the structure of the pressure detecting portion in the capacitive pressure sensor can suppress degradation of accuracy in measurement due to the above-described misalignment. As a result, they have conceived an idea of configuring the capacitive pressure sensor to have capacitive elements arranged in a staggered or zigzag manner when the sensing surface is seen in two dimensions, so as to increase the sensor density in the direction crossing the extending direction of the artery. In a conventional capacitive pressure sensor having the upper and lower electrodes arranged in rows and columns, however, it would be difficult to arrange the capacitive elements in a staggered manner if the electrodes are arranged orthogonal to each other.

The inventors then found that, even in the case where the one electrodes arranged in rows are formed of strip-shaped electrodes extending substantially linearly in approximately parallel with each other, if the other electrodes arranged in columns are changed in shape, layout or the like such that the intersections of the one and the other electrodes are offset for each row to form a staggered pattern, then it will be possible to increase the sensor density in the direction parallel to the extending direction of the above-described one electrodes of the capacitive elements. The inventors have found this and come to complete the present invention. More specifically, they have found that even in the case of the capacitive pressure sensor, the capacitive elements can be arranged in a staggered manner either by forming the above-described other electrodes with non-linear strip electrodes of bent shape, stepped shape, S shape or the like and arranging them in columns in parallel with each other, or by forming the other electrodes with linear strip electrodes and arranging them in columns in parallel but with a slope such that they are not orthogonal to the above-described one electrodes.

When the capacitive pressure sensor with such a configuration is brought to practical use as the pressure pulse wave sensor, the pressure pulse wave can be measured with required accuracy. That is, even in the case where the capacitive pressure sensor is used as the pressure pulse wave sensor, the sensor density in the direction crossing the axis of the artery can be increased sufficiently in relation to the diameter of the artery, and accordingly, it is possible to reduce the error caused by the misalignment. Further, when the capacitive elements of the pressure sensor are arranged in a staggered manner, the probability of the capacitive element closest to the central position of the artery being positioned completely within the area corresponding to the flattened part of the artery increases. Thus, it becomes possible to detect only the pressure pulse wave components accurately, without sensing the tension components occurring in the part of the artery other than the flattened part.

Accordingly, the pressure pulse wave can be measured with high accuracy by pressing the sensing surface of the capacitive pressure pulse wave sensor against the approximate position of the artery, instead of exactly positioning the pressure sensor with respect to the artery.

Hereinafter, preferable embodiments of the present invention having been completed through the above-described investigation will be described in detail with reference to the drawings.

First Embodiment

Figure 2:
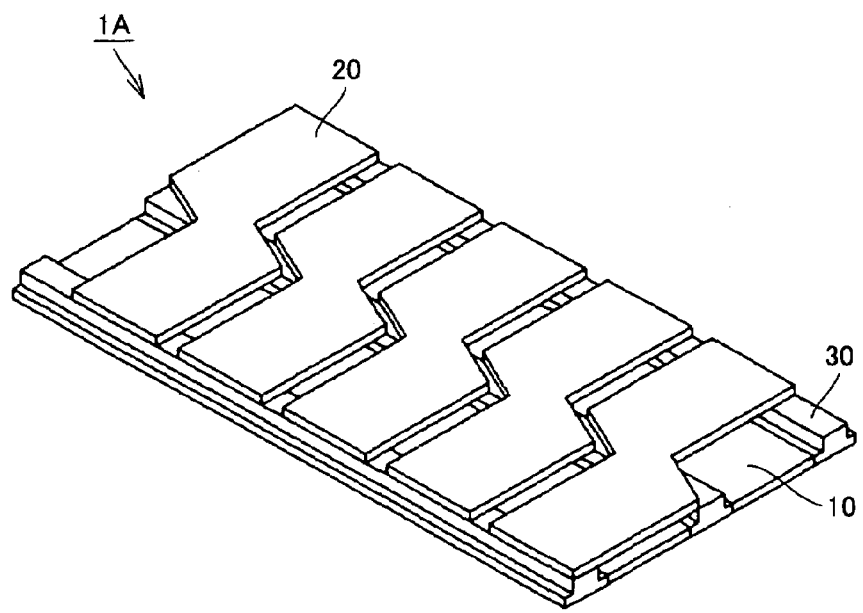
FIG. 2 is a perspective view of a pressure detecting portion of an array-type capacitive pressure pulse wave sensor according to a first embodiment of the present invention.
Figure 3:
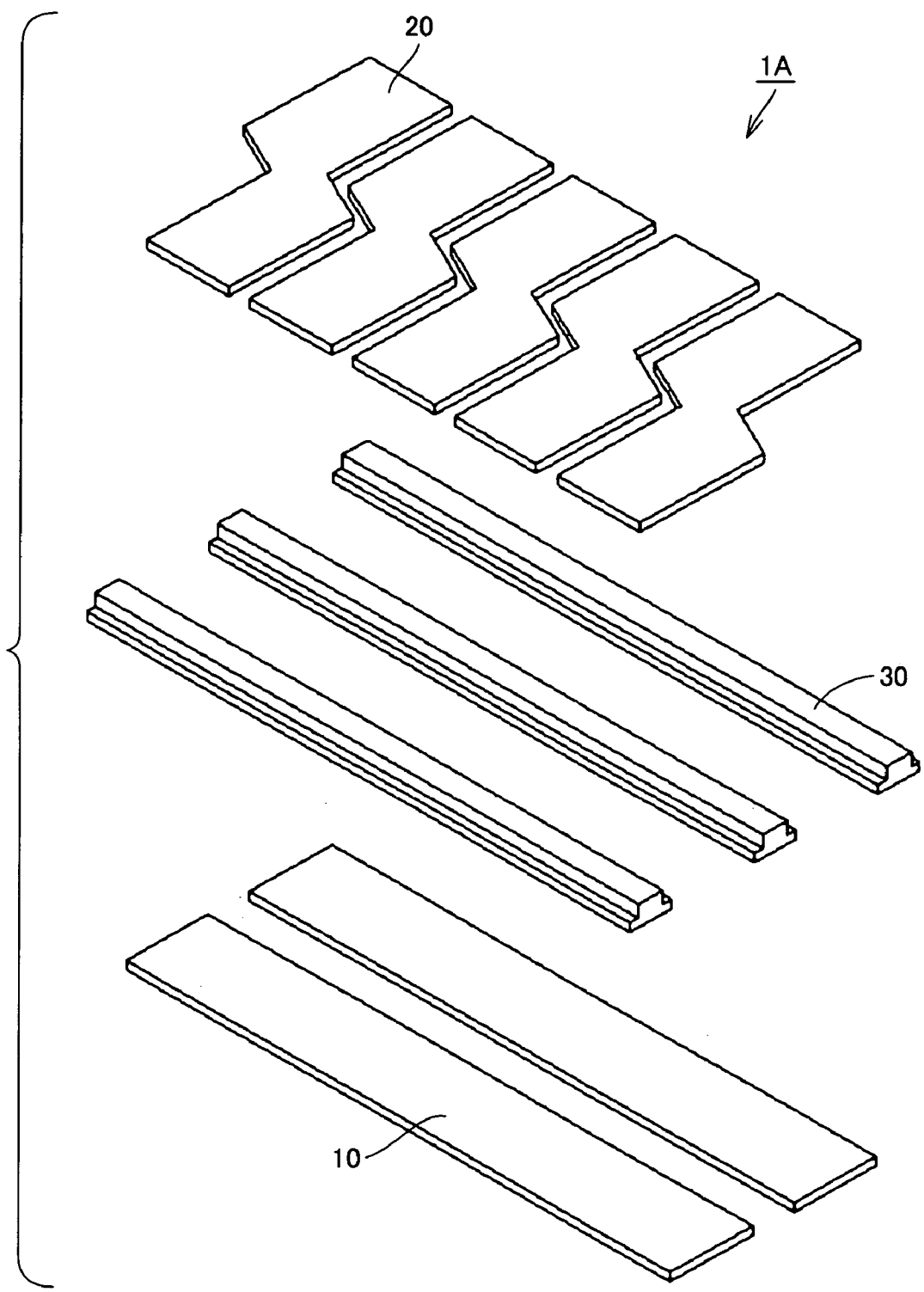
FIG. 3 is an exploded perspective view of the pressure detecting portion shown in FIG. 2.
Figure 4A:
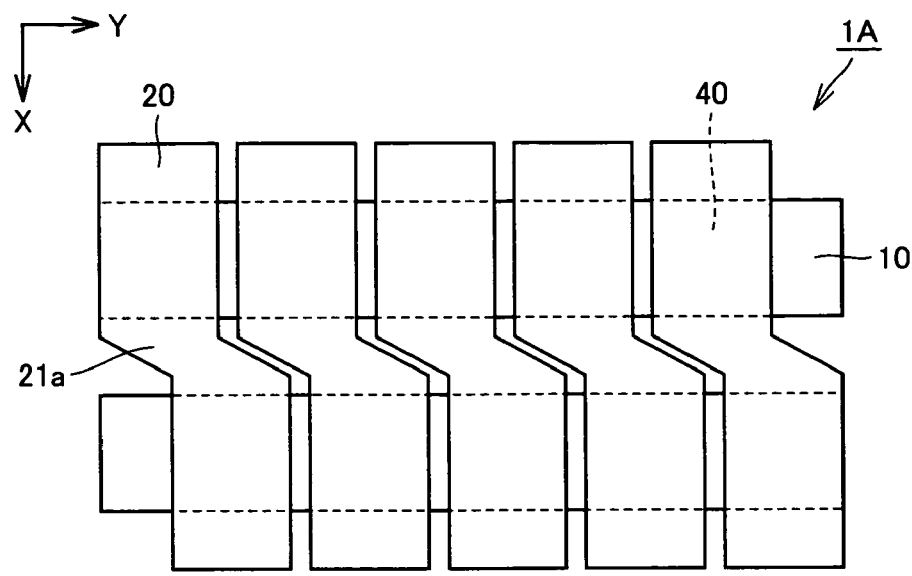
FIG. 4A is a plan view of the pressure detecting portion shown in FIG. 2 as seen from the above.
Figure 4B:
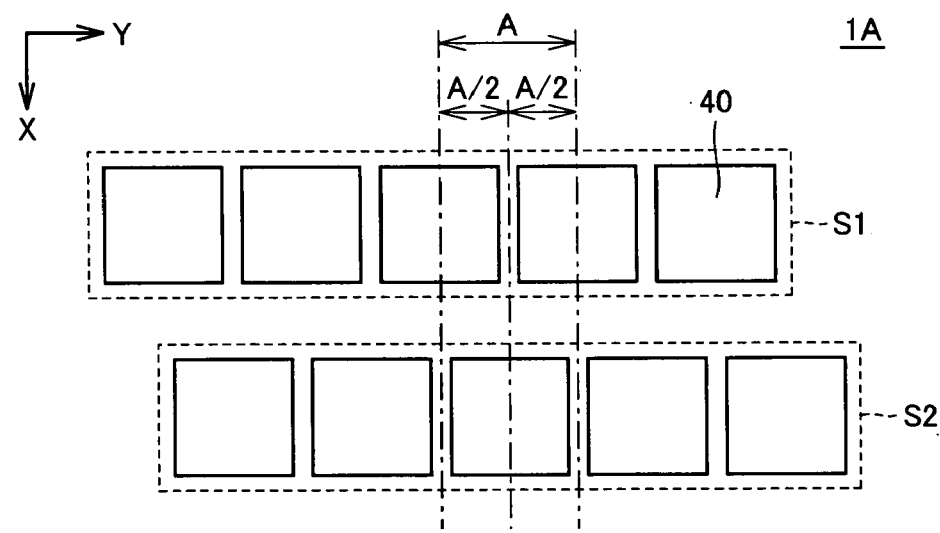
FIG. 4B is a schematic diagram showing a layout of capacitive elements in the pressure detecting portion shown in FIG. 2.

FIG. 2 is a perspective view of a pressure detecting portion of an array-type capacitive pressure pulse wave sensor according to the first embodiment of the present invention, and FIG. 3 is an exploded perspective view of the pressure detecting portion shown in FIG. 2. FIG. 4A is a plan view of the pressure detecting portion of FIG. 2 when seen from the above, and FIG. 4B is a schematic diagram showing a layout of capacitive elements in the pressure detecting portion shown in FIG. 2.

As shown in FIGS. 2 and 3, the array-type capacitive pressure pulse wave sensor 1A of the present embodiment primarily includes lower electrodes 10 as the first electrodes, upper electrodes 20 as the second electrodes, and spacer members 30 arranged between lower electrodes 10 and upper electrodes 20. Lower electrodes 10 are m rows (m is a natural number of more than 1, here, m=2) of strip-shaped electrodes that extend substantially linearly and are arranged parallel to each other. Upper electrodes 20 are n columns (n is a natural number of more than 1, here, n=5) of strip-shaped electrodes that extend parallel to each other. Lower electrodes 10 and upper electrodes 20 are formed of copper strips, for example, and are spaced apart from each other with a prescribed distance in the vertical direction secured by spacer members 30 of silicon rubber or the like.

As shown in FIG. 4A, each of lower electrodes 10 is arranged to extend in the direction (Y direction in the figure) approximately orthogonal to the direction (X direction in the figure) in which the artery extends, at the time of measurement. Each of upper electrodes 20 is arranged to extend in the direction crossing the direction (Y direction in the figure) in which lower electrodes 10 extend.

As shown in FIG. 4A, each upper electrode 20 is provided with a bent portion 21a at a prescribed position. More specifically, bent portion 21a is provided at a part of upper electrode 20 located between lower electrodes 10 and not overlapping either of lower electrodes 10 when the pressure detecting portion of array-type capacitive pressure pulse wave sensor 1A is seen in two dimensions. The bent portion is bent in the direction crossing the extending direction (X direction in the figure) of the artery. Thus, when the pressure detecting portion of array-type capacitive pressure pulse wave sensor 1A is seen in two dimensions, the intersections of one upper electrode 20 with lower electrodes 10 are formed offset for each row in the extending direction (Y direction in the figure) of lower electrodes 10.

At the intersections of lower electrodes 10 and upper electrodes 20 arranged in rows and columns, lower electrodes 10 and upper electrodes 20 are arranged at a prescribed distance (of about 100 μm, for example) from each other by spacer members 30 of silicon rubber or the like. A part of upper electrode 20 and a part of lower electrode 10 face each other at each intersection, and m×n (here, a total of 10) capacitive elements 40 serving as the sensor elements are formed at the intersections.

As shown in FIG. 4B, in array-type capacitive pressure pulse wave sensor 1A of the present embodiment, a capacitive element group S1 formed on lower electrode 10 of the first row located at the upper level in the figure and a capacitive element group S2 formed on lower electrode 10 of the second row located at the lower level in the figure are arranged offset from each other in the direction (Y direction in the figure) orthogonal to the extending direction (X direction in the figure) of the artery. Thus, when the pressure detecting portion is seen in two dimensions, capacitive elements 40 are arranged in a staggered manner. This results from upper electrodes 20 provided with bent portions 21a at prescribed positions. It is noted that, in array-type capacitive pressure pulse wave sensor 1A of the present embodiment, when the distance between the central positions of capacitive elements 40 adjacent to each other in the Y direction in the figure is represented by A, capacitive element group S1 formed on the first-row lower electrode 10 and capacitive element group S2 formed on the second-row lower electrode 20 are arranged with an offset of A/2 from each other in the Y direction in the figure.

Figure 16:
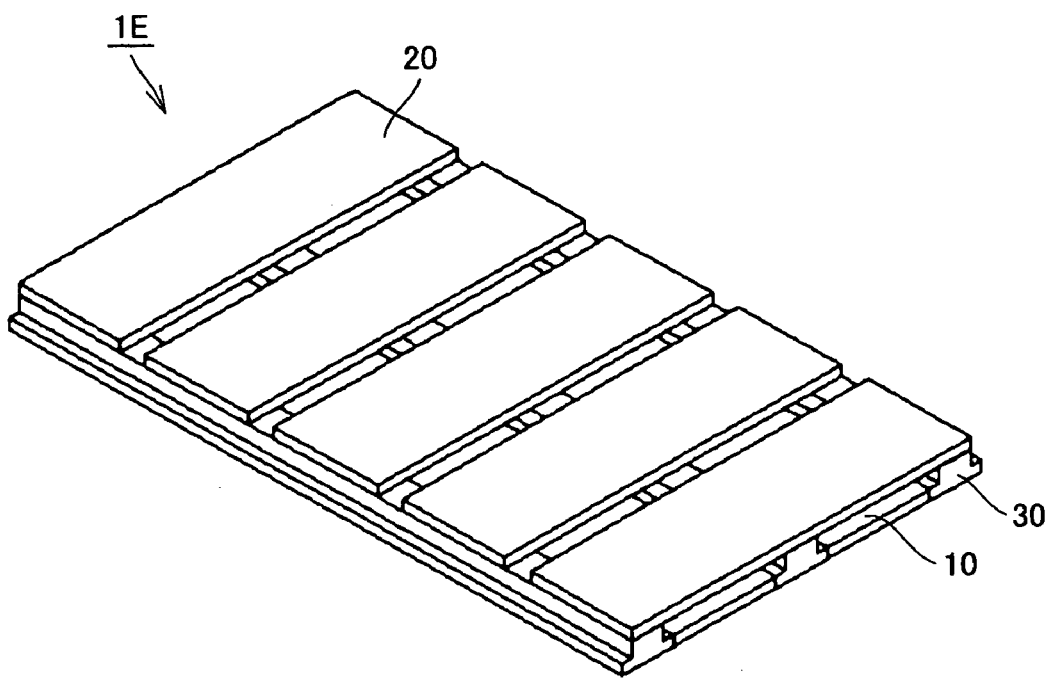
FIG. 16 is a perspective view of a pressure detecting portion of a conventional pressure sensor of capacitive type.
Figure 17:
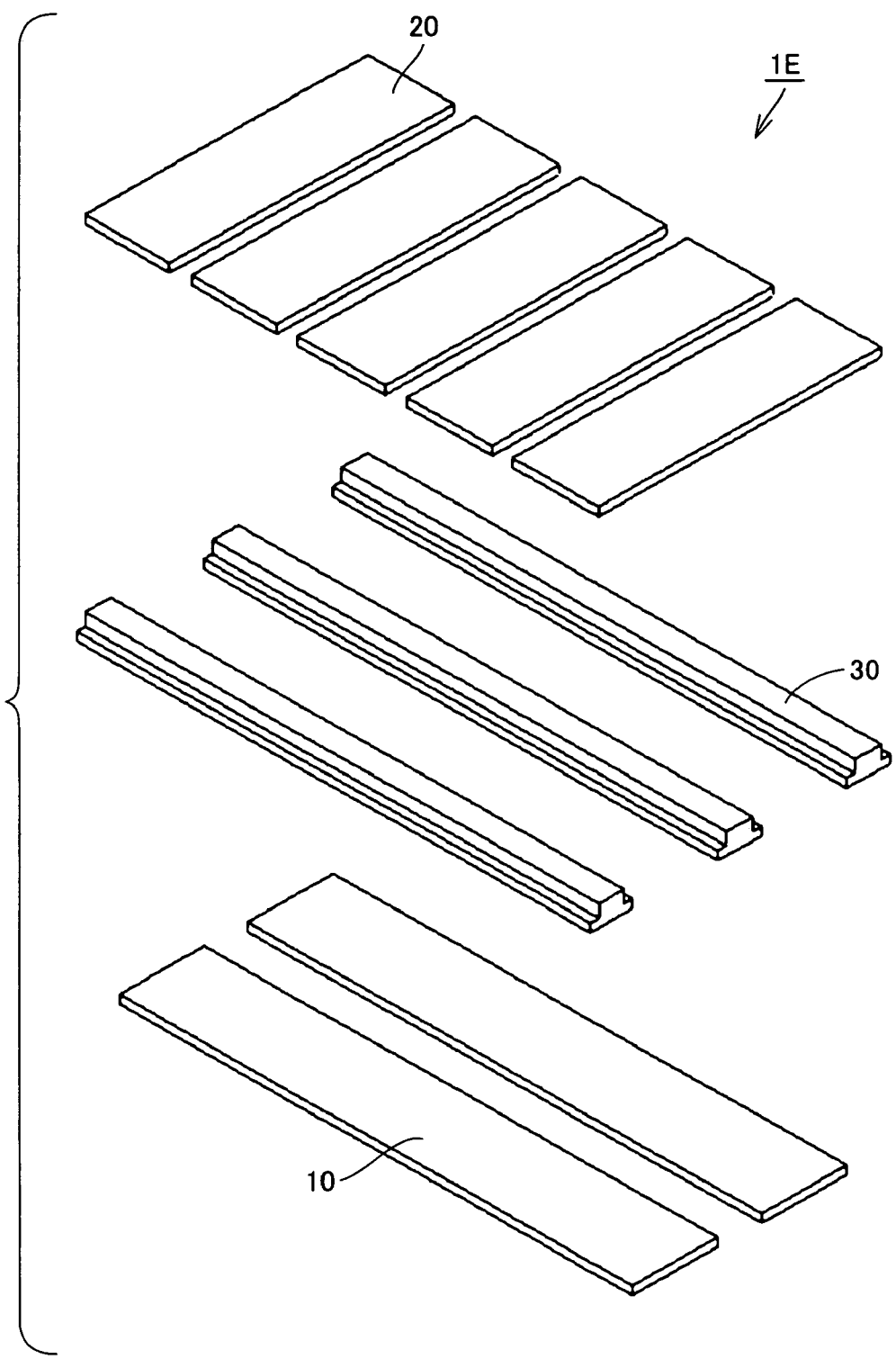
FIG. 17 is an exploded perspective view of the pressure detecting portion shown in FIG. 16.
Figure 18A:
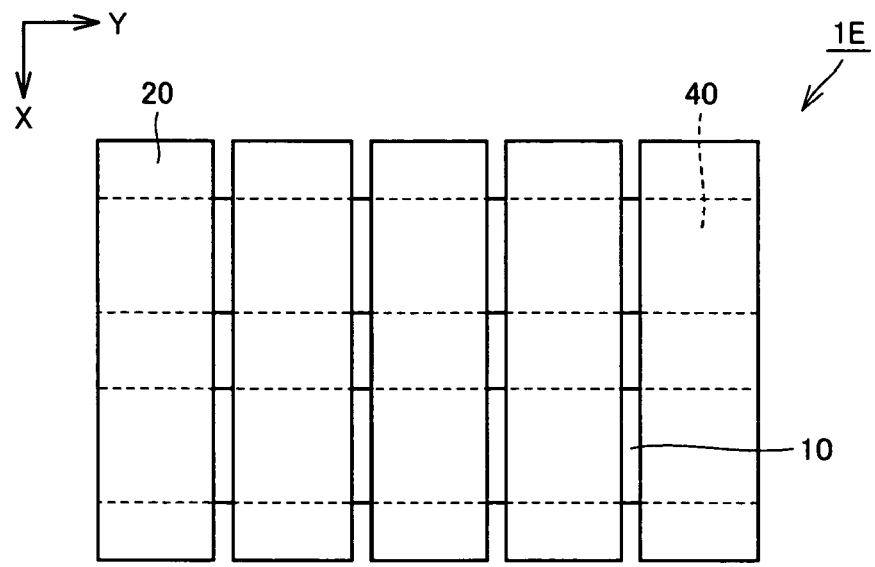
FIG. 18A is a plan view of the pressure detecting portion shown in FIG. 16 as seen from the above.
Figure 18B:
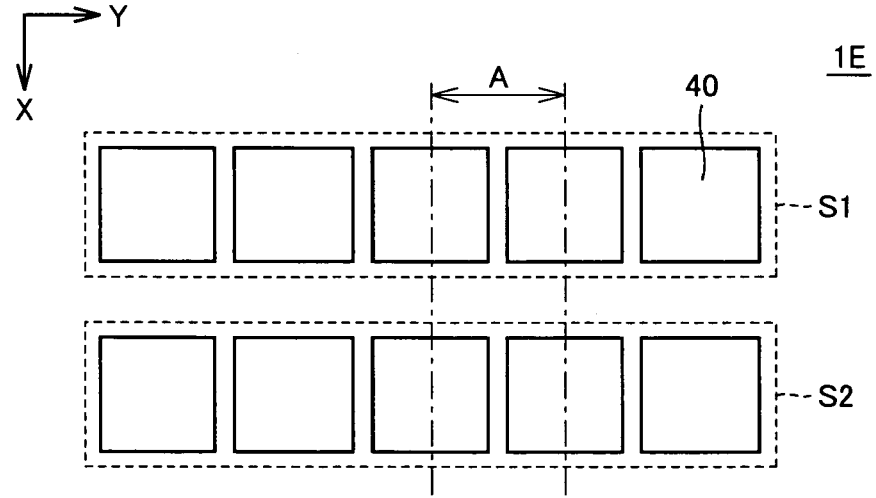
FIG. 18B is a schematic diagram showing a layout of capacitive elements in the pressure detecting portion shown in FIG. 16.

Such a layout of capacitive element group S1 and capacitive element group S2 offset from each other in the Y direction in the figure can increase the sensor density in the direction orthogonal to the extending direction of the artery. If upper electrodes 20 are formed linearly, similarly to lower electrodes 10, and lower electrodes 10 and upper electrodes 20 are arranged orthogonal to each other, i.e., if the sensor elements (capacitive elements) have the layout (see FIG. 18B) as in the case of the above-described conventional pressure sensor 1E (see FIGS. 16 and 18B), then the misalignment between the central position of the artery and the central position of the sensor element located closest to the central position of the artery at the time of measurement will be A/2 at a maximum. By comparison, in the case of the layout (see FIG. 4B) according to the present embodiment, the above-described misalignment is A/4 at a maximum. Accordingly, it is possible to measure the pressure pulse wave accurately and stably compared to the conventional case.

Figure 19:
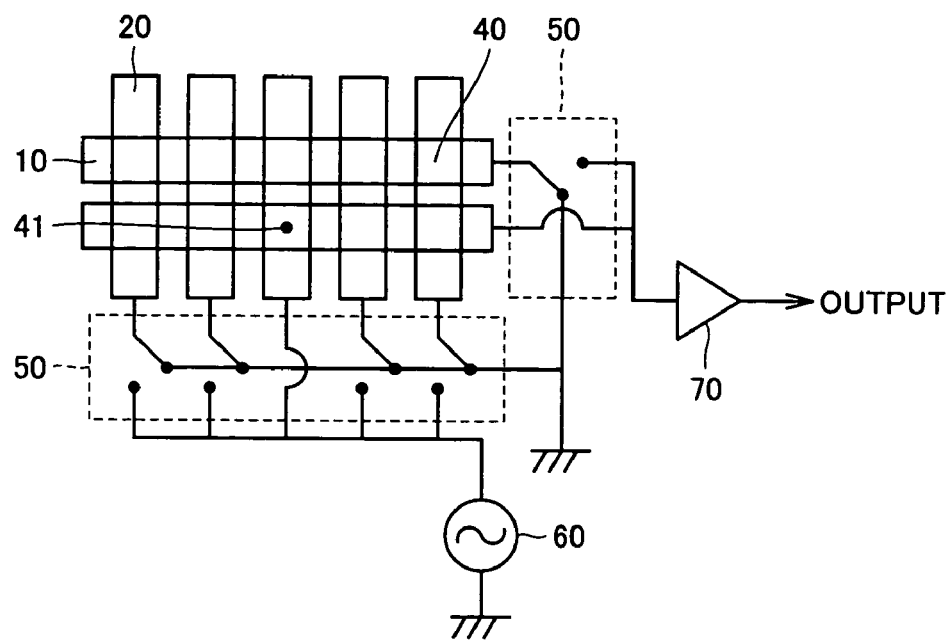
FIG. 19 is a circuit configuration diagram of a capacitive pressure sensor including the pressure detecting portion shown in FIG. 16.

Further, in array-type capacitive pressure pulse wave sensor 1A of the present embodiment, the microfabrication technique currently available for the capacitive type pressure sensor can be adapted, without the need of an advanced microfabrication technique. Thus, it is possible to produce the pressure pulse wave sensor inexpensively. It is noted that the circuit configuration of the capacitive pressure pulse wave sensor of the present embodiment is identical to that of the conventional one shown in FIG. 19.

When the layout of the sensor elements as in the present embodiment (i.e., the layout shown in FIG. 4B) is employed, the increased sensor density in the Y direction in the figure can suppress the misalignment to about 0.25 mm to 0.5 mm at a maximum. Thus, it is expected that the error in the AI value will be restricted to about 0.5% at a maximum, as seen from FIG. 1. This is a sufficiently low level enabling its practical use as the pressure pulse wave sensor.

As described above, according to the array-type capacitive pressure pulse wave sensor of the present embodiment, the pressure pulse wave can be measured more accurately and more stably than in the case of using the conventional capacitive type pressure sensor. Accordingly, the capacitive type pressure sensor producible at a low price can be used as the pressure pulse wave sensor, enabling considerable reduction of manufacturing cost.

Second Embodiment

Figure 5:
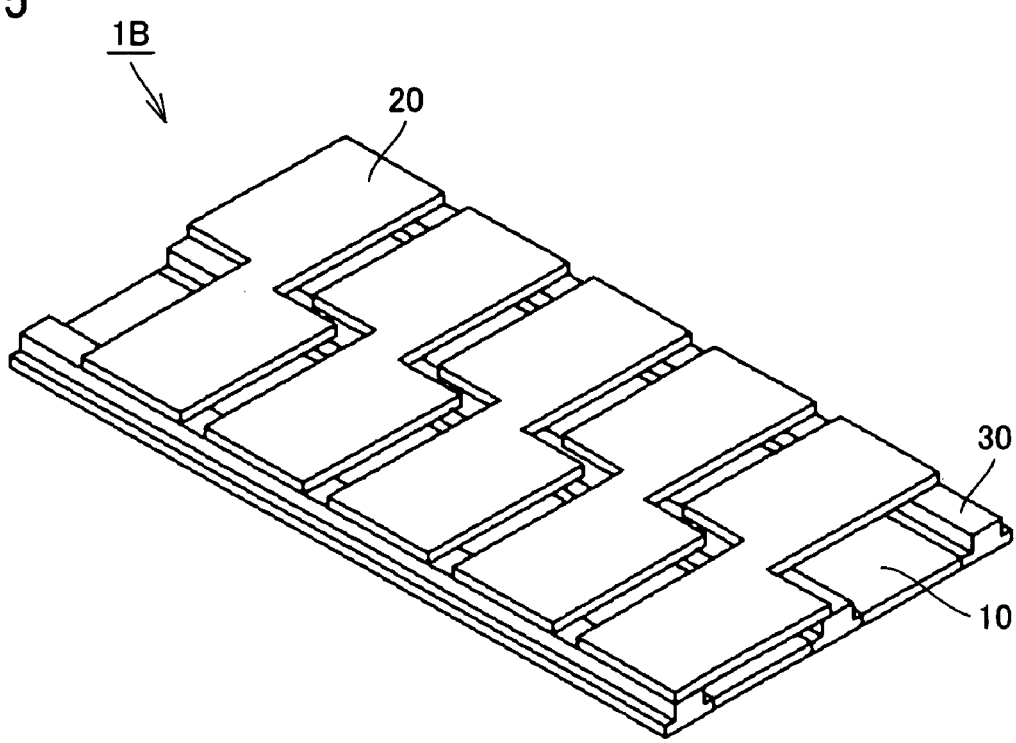
FIG. 5 is a perspective view of a pressure detecting portion of an array-type capacitive pressure pulse wave sensor according to a second embodiment of the present invention.
Figure 6:
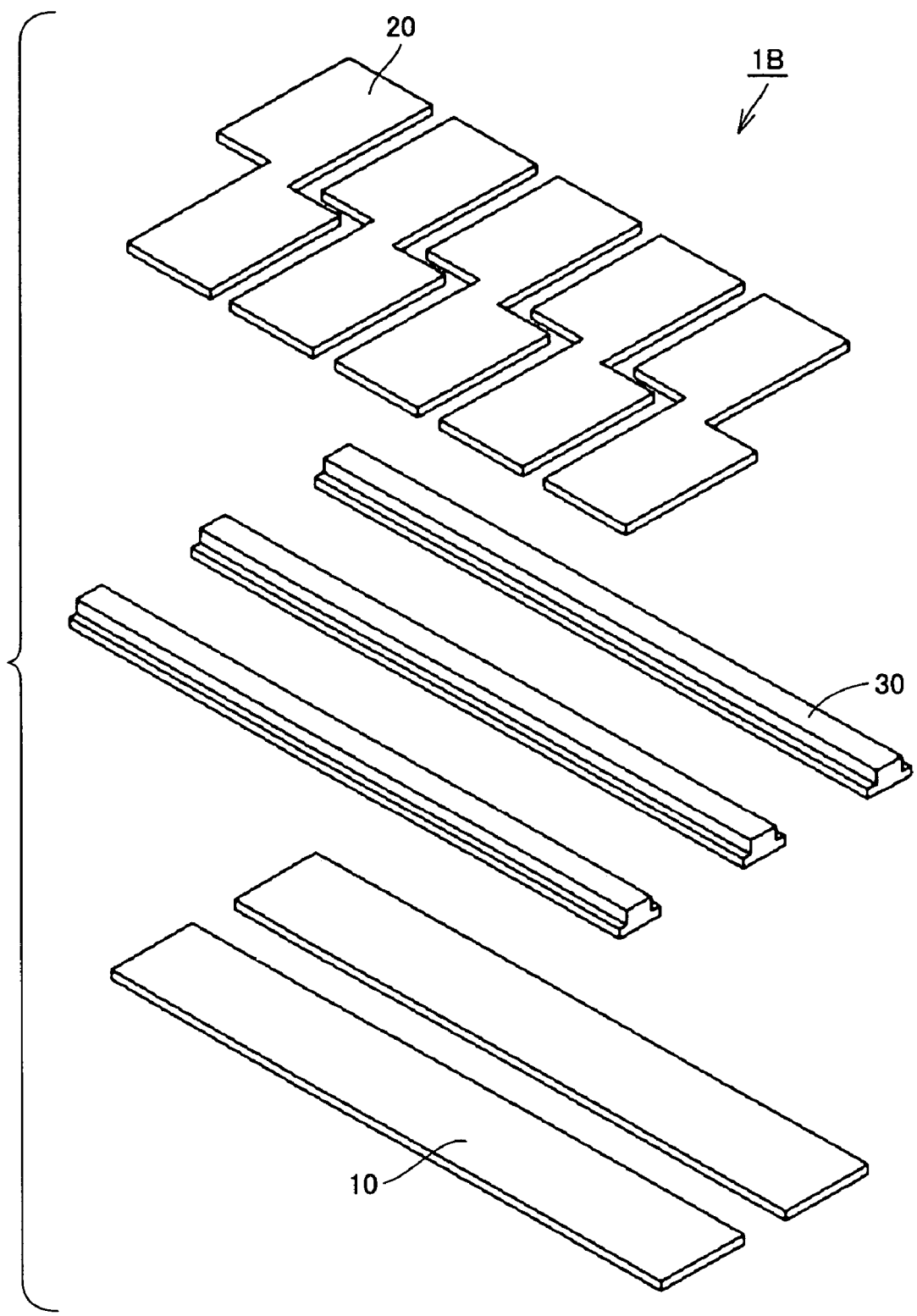
FIG. 6 is an exploded perspective view of the pressure detecting portion shown in FIG. 5.
Figure 7A:
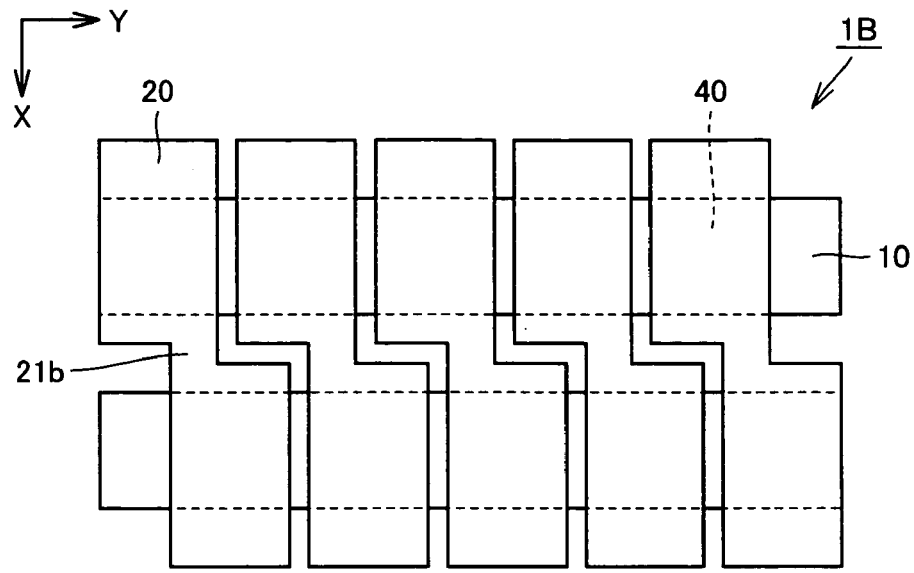
FIG. 7A is a plan view of the pressure detecting portion shown in FIG. 5 as seen from the above.
Figure 7B:
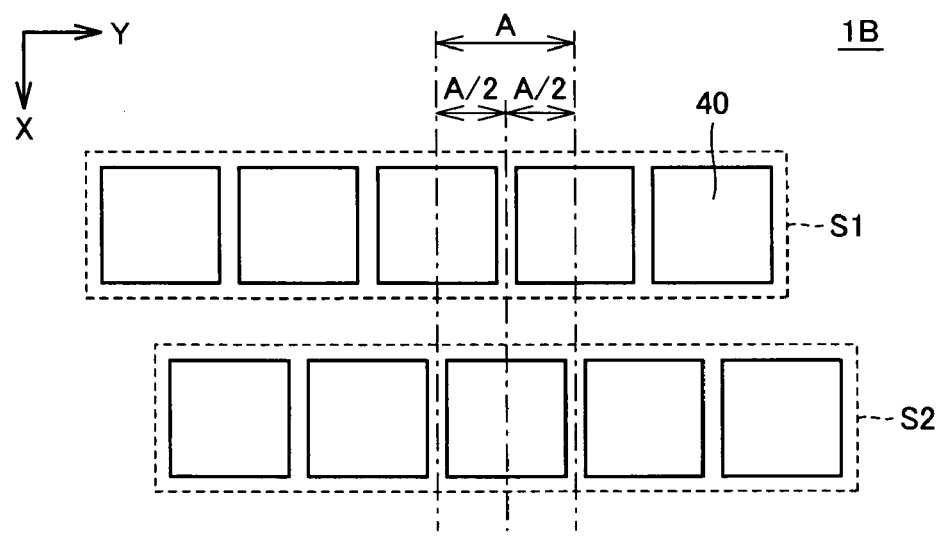
FIG. 7B is a schematic diagram showing a layout of capacitive elements in the pressure detecting portion shown in FIG. 5.

FIG. 5 is a perspective view of a pressure detecting portion of an array-type capacitive pressure pulse wave sensor according to a second embodiment of the present invention. FIG. 6 is an exploded perspective view of the pressure detecting portion shown in FIG. 5. FIG. 7A is a plan view of the pressure detecting portion of FIG. 5 as seen from the above, and FIG. 7B is a schematic diagram showing a layout of capacitive elements in the pressure detecting portion shown in FIG. 5. The like portions as in the first embodiment are denoted by the like reference characters, and description thereof will not be repeated.

As shown in FIGS. 5 and 6, the array-type capacitive pressure pulse wave sensor 1B of the present embodiment primarily includes lower electrodes 10 as the first electrodes, upper electrodes 20 as the second electrodes, and spacer members 30 arranged between lower electrodes 10 and upper electrodes 20, as in the case of array-type capacitive pressure pulse wave sensor 1A of the first embodiment.

As shown in FIG. 7A, lower electrodes 10 are two rows of strip-shaped electrodes that are arranged in parallel with each other to extend substantially linearly in the direction (Y direction in the figure) approximately orthogonal to the direction (X direction in the figure) in which the artery extends, at the time of measurement. Upper electrodes 20 are five columns of strip-shaped electrodes arranged in parallel with each other to extend in the direction crossing the direction (Y direction in the figure) in which lower electrodes 10 extend. Lower electrodes 10 and upper electrodes 20 are formed of copper strips, for example, and they are spaced apart from each other by a prescribed distance in the vertical direction secured by spacer members 30 of silicon rubber or the like (see FIGS. 5 and 6).

As shown in FIG. 7A, each of upper electrodes 20 is provided with a bent portion 21b at a prescribed position. More specifically, when the pressure detecting portion of array-type capacitive pressure pulse wave sensor 1B is seen in two dimensions, bent portion 21b is provided at a part of upper electrode 20 located between lower electrodes 10 and not overlapping either of lower electrodes 10. The upper intersections of upper electrodes 20 with lower electrode 10 of the first row located at the upper level in the figure and the lower intersections of upper electrodes 20 with lower electrode 10 of the second row located at the lower level in the figure are offset from each other in the direction (Y direction in the figure) orthogonal to the extending direction (X direction in the figure) of the artery, with the above-described bent portions 21b connecting the upper intersections and the lower intersections. With this configuration, when the pressure detecting portion of array-type capacitive pressure pulse wave sensor 1B is seen in two dimensions, the intersections of one upper electrode 20 and lower electrodes 10 are formed offset for each row in the extending direction (Y direction in the figure) of lower electrodes 10.

At the intersections of lower electrodes 10 and upper electrodes 20 arranged in rows and columns, lower electrodes 10 and upper electrodes 20 are arranged at a prescribed distance from each other by spacer members 30 of silicon rubber or the like. As such, a part of upper electrode 20 and a part of lower electrode 10 are arranged to face each other at each intersection, thereby forming a capacitive element 40 serving as the sensor element.

With this configuration as well, capacitive elements 40 are arranged in a staggered manner when the pressure detecting portion is seen in two dimensions, as in the case of capacitive pressure pulse wave sensor 1A of the first embodiment. Accordingly, the effects similar to those in the first embodiment can be obtained.

Third Embodiment

Figure 8:
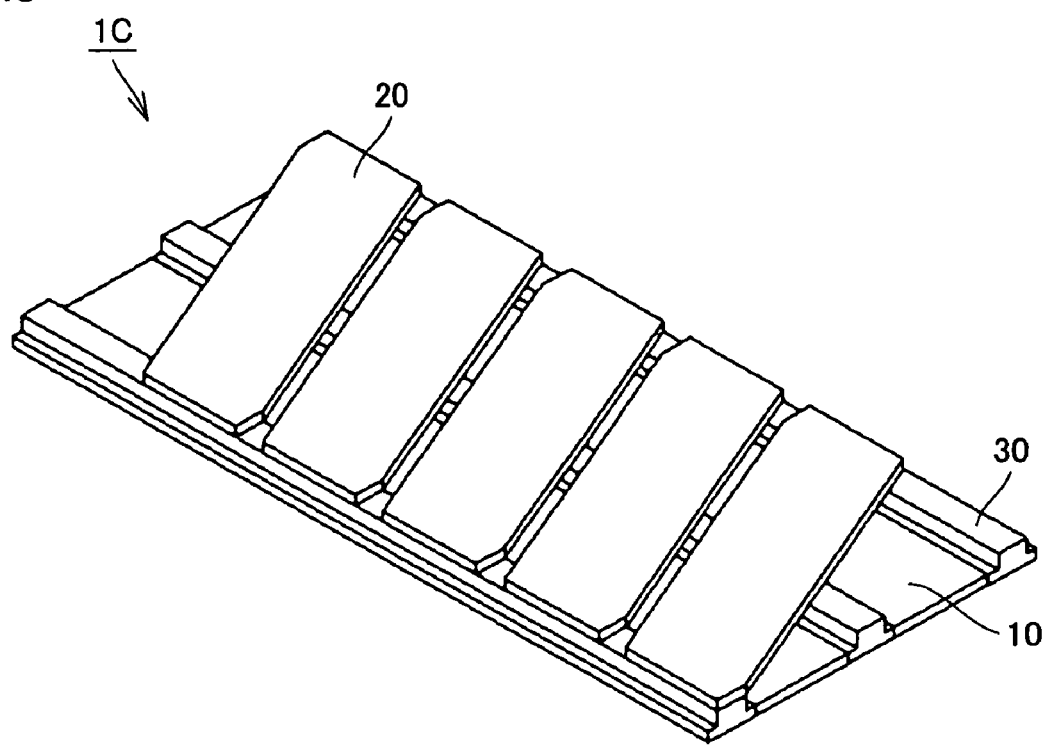
FIG. 8 is a perspective view of a pressure detecting portion of an array-type capacitive pressure pulse wave sensor according to a third embodiment of the present invention.
Figure 9:
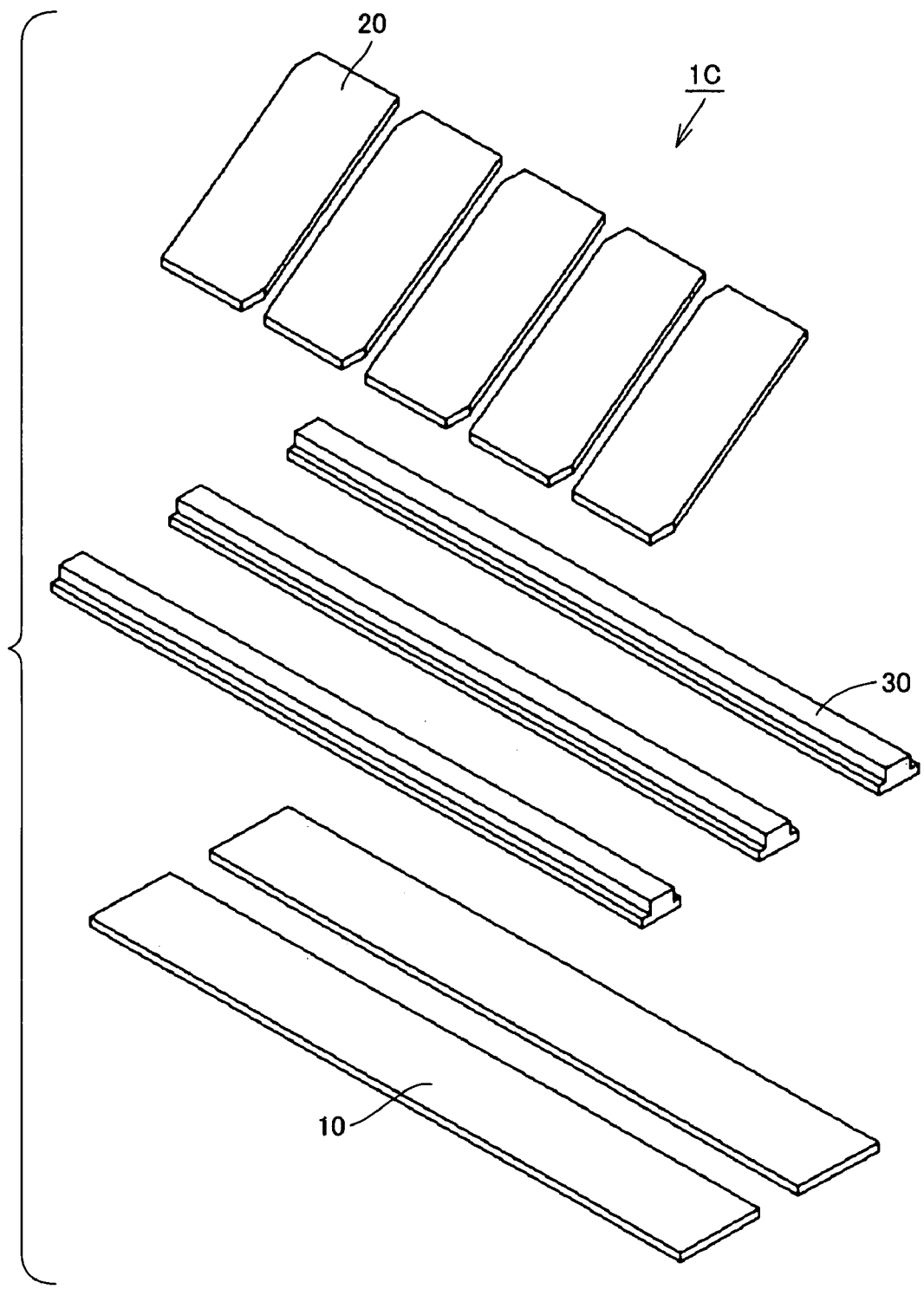
FIG. 9 is an exploded perspective view of the pressure detecting portion shown in FIG. 8.
Figure 10A:
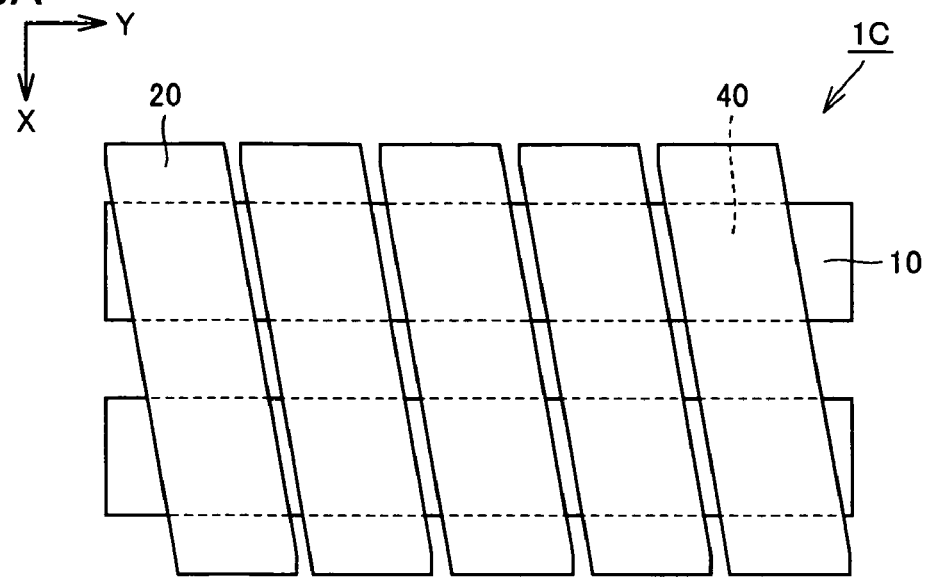
FIG. 10A is a plan view of the pressure detecting portion shown in FIG. 8 as seen from the above.
Figure 10B:
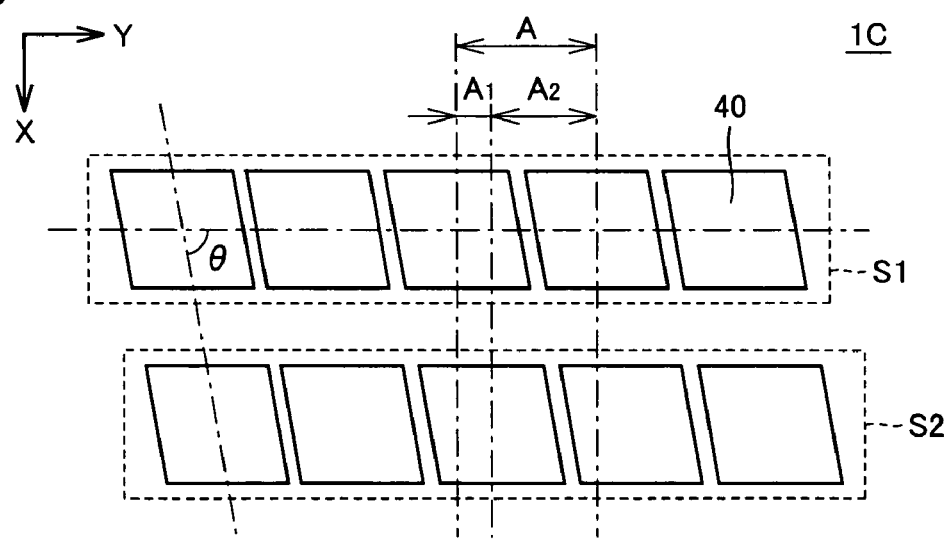
FIG. 10B is a schematic diagram showing a layout of capacitive elements in the pressure detecting portion shown in FIG. 8.

FIG. 8 is a perspective view of a pressure detecting portion of an array-type capacitive pressure pulse wave sensor according to the third embodiment of the present invention, and FIG. 9 is an exploded perspective view thereof. FIG. 10A is a plan view of the pressure detecting portion shown in FIG. 8, and FIG. 10B is a schematic diagram showing a layout of capacitive elements in the pressure detecting portion of FIG. 8. The like portions as in the first embodiment are denoted by the like reference characters, and description thereof will not be repeated.

As shown in FIGS. 8 and 9, the array-type capacitive pressure pulse wave sensor 1C of the present embodiment primarily includes lower electrodes 10 as the first electrodes, upper electrodes 20 as the second electrodes, and spacer members 30 arranged between lower electrodes 10 and upper electrodes 20, as in the case of array-type capacitive pressure pulse wave sensor 1A of the first embodiment.

As shown in FIG. 10A, lower electrodes 10 are two rows of strip-shaped electrodes that are arranged in parallel with each other to extend substantially linearly in the direction (Y direction in the figure) approximately orthogonal to the extending direction (X direction in the figure) of the artery. Upper electrodes 20 are five columns of strip-shaped electrodes that are arranged in parallel with each other to extend substantially linearly in the direction not orthogonal to the extending direction (Y direction in the figure) of lower electrodes 10. Lower electrodes 10 and upper electrodes 20 are formed of copper strips, for example, and are arranged at a prescribed distance in the vertical direction by provision of spacer members 30 of silicon rubber or the like (see FIGS. 8 and 9).

As shown in FIG. 10A, at the intersections of lower electrodes 10 and upper electrodes 20 arranged in rows and columns, lower electrodes 10 and upper electrodes 20 are at the prescribed distance from each other via spacer members 30 of silicon rubber or the like. As such, a part of upper electrode 20 and a part of lower electrode 10 are arranged to face each other at each intersection, thereby constituting a capacitive element 40 serving as the sensor element.

As shown in FIG. 10B, by making substantially linear lower electrodes 10 and substantially linear upper electrodes 20 cross each other not orthogonally as in capacitive pressure pulse wave sensor 1C of the present embodiment, the capacitive element group S1 formed on lower electrode 10 of the first row located at the upper level in the figure and the capacitive element group S2 formed on lower electrode 10 of the second row located at the lower level in the figure can be arranged offset from each other in the direction (Y direction in the figure) orthogonal to the direction (X direction in the figure) in which the artery extends. The amount of offset between capacitive element group S1 and capacitive element group S2 is determined by a crossing angle θ of lower electrodes 10 and upper electrodes 20. Thus, distances A1 and A2 representing the amounts of offset between the central positions of capacitive elements 40 can be set to desired values by changing the crossing angle θ as appropriate.

With this configuration as well, capacitive elements 40 can be arranged in a staggered manner when the pressure detecting portion is seen in two dimensions, as in the case of capacitive pressure pulse wave sensor 1A of the first embodiment, and thus, similar effects to those of the first embodiment can be obtained.

Fourth Embodiment

Figure 11:
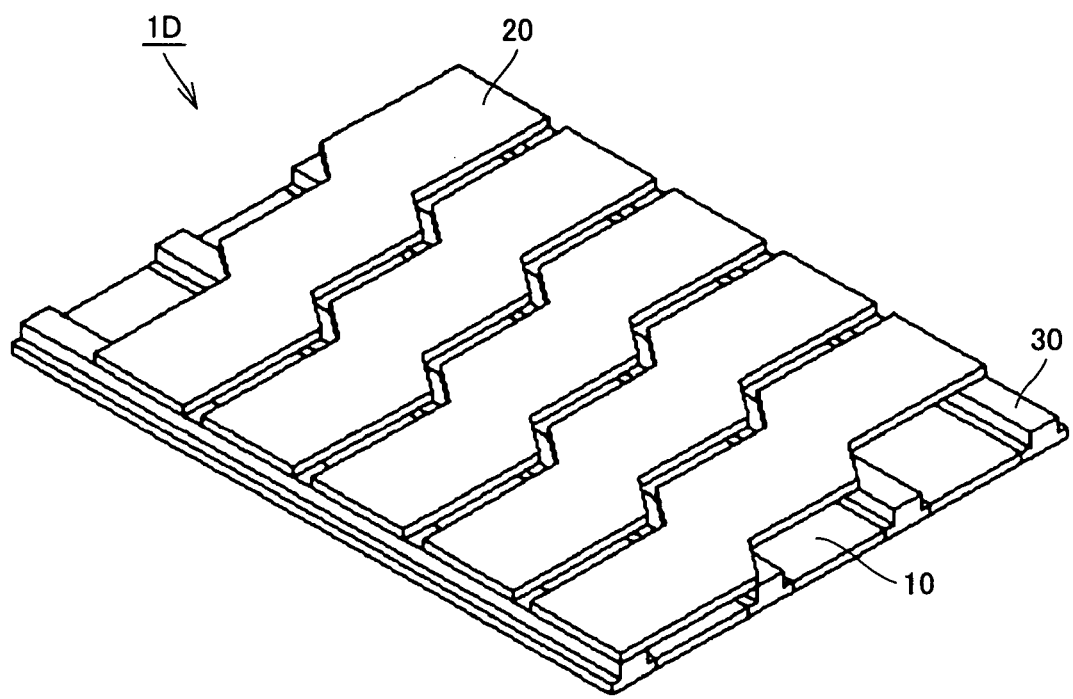
FIG. 11 is a perspective view of a pressure detecting portion of an array-type capacitive pressure pulse wave sensor according to a fourth embodiment of the present invention.
Figure 12:
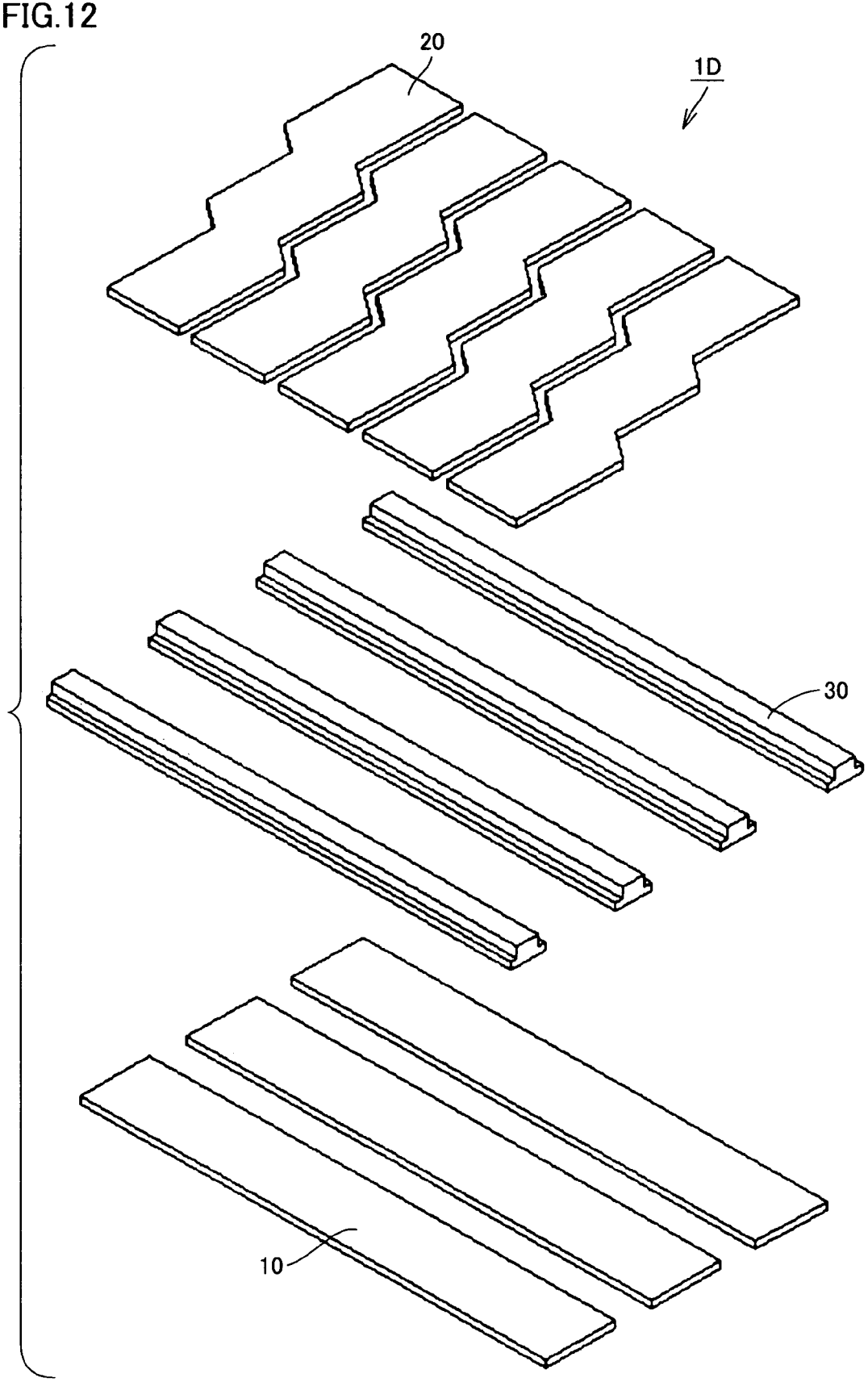
FIG. 12 is an exploded perspective view of the pressure detecting portion shown in FIG. 11.
Figure 13A:
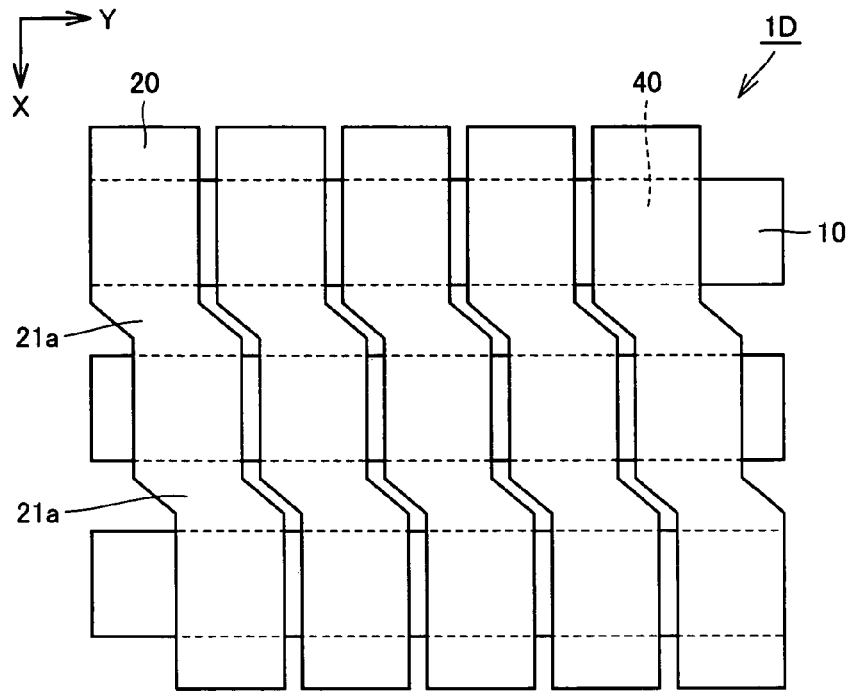
FIG. 13A is a plan view of the pressure detecting portion shown in FIG. 11 as seen from the above.
Figure 13B:
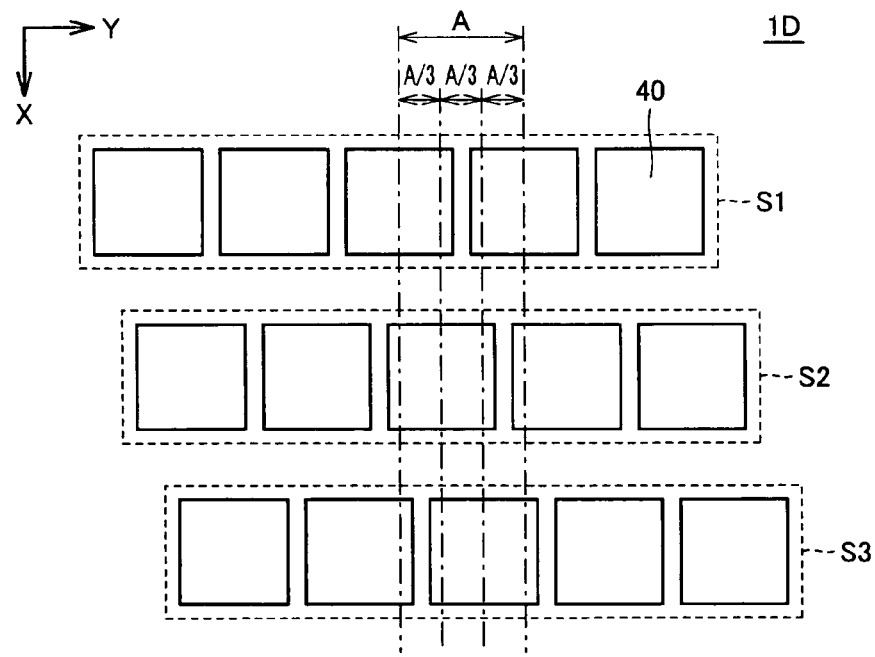
FIG. 13B is a schematic diagram showing a layout of capacitive elements in the pressure detecting portion shown in FIG. 11.

FIG. 11 is a perspective view of a pressure detecting portion of an array-type capacitive pressure pulse wave sensor according to the fourth embodiment of the present invention, and FIG. 12 is an exploded perspective view of the pressure detecting portion shown in FIG. 11. FIG. 13A is a plan view of the pressure detecting portion of FIG. 11 when seen from above, and FIG. 13B is a schematic diagram showing a layout of capacitive elements in the pressure detecting portion of FIG. 11. The like portions as in the first embodiment are denoted by the like reference characters, and description thereof will not be repeated.

As shown in FIGS. 11 and 12, the array-type capacitive pressure pulse wave sensor 1D of the present embodiment primarily includes lower electrodes 10 as the first electrodes, upper electrodes 20 as the second electrodes, and spacer members 30 arranged between lower electrodes 10 and upper electrodes 20, as in the case of array-type capacitive pressure pulse wave sensor 1A of the first embodiment.

As shown in FIG. 13A, lower electrodes 10 are three rows of strip-shaped electrodes that are arranged in parallel with each other to extend substantially linearly in the direction (Y direction in the figure) approximately orthogonal to the direction (X direction in the figure) in which the artery extends, at the time of measurement. Upper electrodes 20 are five columns of strip-shaped electrodes that are arranged in parallel with each other to extend in the direction crossing the direction (Y direction in the figure) in which lower electrodes 10 extend. Lower electrodes 10 and upper electrodes 20 are formed of copper strips, for example, and are arranged at a prescribed distance in the vertical direction by provision of spacer members 30 of silicon rubber or the like therebetween (see FIGS. 11 and 12).

As shown in FIG. 13A, each of upper electrodes 20 is provided with two bent portions 21a. More specifically, each of bent portions 21a is provided at a part of upper electrode 20 located between neighboring two lower electrodes 10 and not overlapping either of the relevant lower electrodes 10 when the pressure detecting portion of array-type capacitive pressure pulse wave sensor 1D is seen in two dimensions. Each bent portion 21a is bent in the direction crossing the extending direction (X direction in the figure) of the artery. As such, when the pressure detecting portion of array-type capacitive pressure pulse wave sensor 1D is seen in two dimensions, the intersections of one upper electrode 20 with lower electrodes 10 are offset for each row in the extending direction (Y direction in the figure) of lower electrode 10.

At the intersections of lower electrodes 10 and upper electrodes 20 arranged in rows and columns, lower electrodes 10 and upper electrodes 20 are at a prescribed distance via spacer member 30 of silicon rubber or the like. With a part of upper electrode 20 and a part of lower electrode 10 facing each other at each intersection, m×n (here, a total of 15) capacitive elements 40 serving as the sensor elements are formed at the intersections.

As shown in FIG. 13B, in array-type capacitive pressure pulse wave sensor 1D according to the present embodiment, a capacitive element group S1 formed on lower electrode 10 of the first row located at the top in the figure, a capacitive element group S2 formed on lower electrode 10 of the second row located in the middle in the figure, and a capacitive element group S3 formed on lower electrode 10 of the third row located at the bottom in the figure, are arranged offset from each other in the direction (Y direction in the figure) orthogonal to the extending direction (X direction in the figure) of the artery. As such, when the pressure detecting portion is seen in two dimensions, capacitive elements 40 are arranged in a staggered manner, as a result of provision of two bent portions 21a for each of upper electrodes 20 at prescribed positions. In array-type capacitive pressure pulse wave sensor 1D of the present embodiment, when the distance between the central positions of neighboring capacitive elements 40 in the Y direction in the figure is represented by A, capacitive element group S1 on the first-row lower electrode 10 at the top and capacitive element group S2 on the second-row lower electrode 10 in the middle are arranged with an offset of A/3 from each other in the Y direction in the figure, and capacitive element group S2 on the second-row lower electrode 10 in the middle and capacitive element group S3 on the third-row lower electrode 10 at the bottom are arranged with an offset of A/3 from each other in the Y direction.

With this configuration as well, capacitive elements 40 are arranged in the staggered manner when the pressure detecting portion is seen in two dimensions, as in the case of capacitive pressure pulse wave sensor 1A of the first embodiment. Accordingly, the effects similar to those in the first embodiment can be obtained.

Further, when the layout as in the present embodiment (shown in FIG. 13B) is adapted, the sensor density in the Y direction is further increased compared to the case of capacitive pressure pulse wave sensor 1A of the first embodiment. More specifically, as explained in conjunction with the first embodiment, assuming that the best microfabrication technique currently available is employed, misalignment between the central position of the artery and the central position of the nearest sensor element in the Y direction in the figure that would occur when adapting the layout shown in FIG. 4B is about 0.25 mm to 0.5 mm at a maximum. In contrast, when the layout as in the present embodiment (shown in FIG. 13B) is adapted, the misalignment will be suppressed to about 0.17 mm to 0.33 mm at a maximum. Thus, as seen from FIG. 1, the error included in the AI value will be restricted to about 0.25% at a maximum. This is a sufficiently low level enabling its practical use as the pressure pulse wave sensor.

Fifth Embodiment

Figure 14:
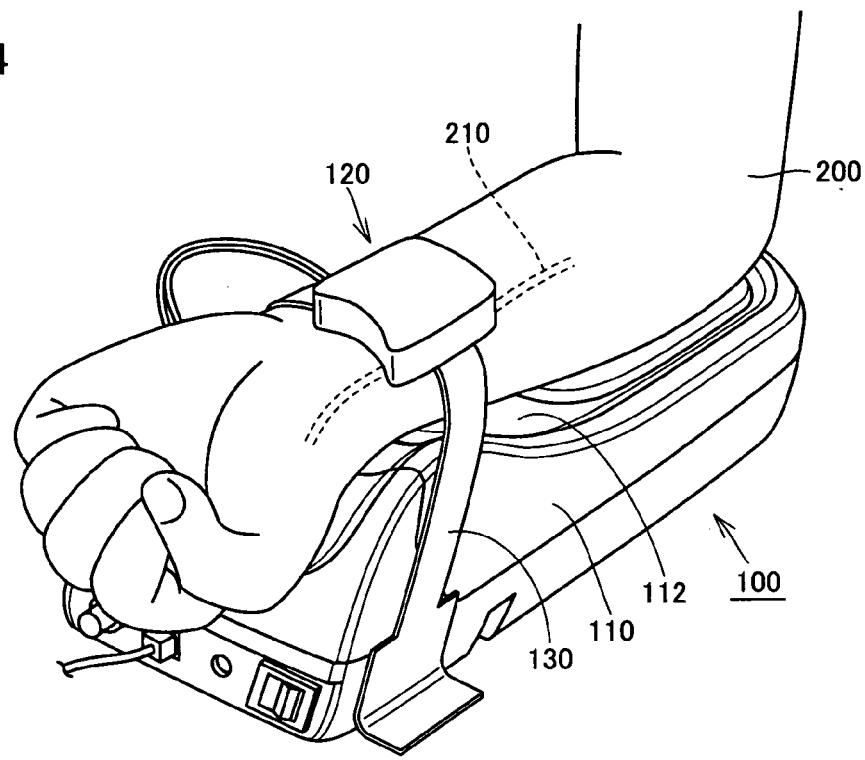
FIG. 14 shows a pulse wave measuring apparatus according to a fifth embodiment of the present invention, in the state of being pressed against a wrist.
Figure 15:
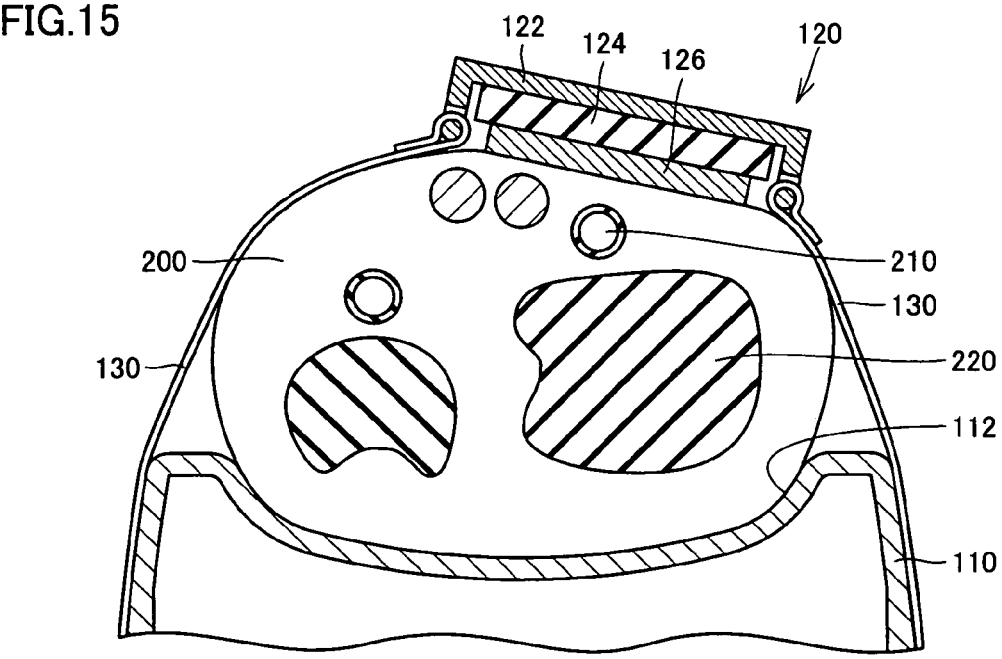
FIG. 15 is a schematic cross sectional view of the wrist and the pulse wave measuring apparatus in the state of measurement as shown in FIG. 14.

A configuration example where the array-type capacitive pressure pulse wave sensor according to any of the first through fourth embodiments of the present invention is incorporated into a pulse wave measuring apparatus will now be explained. FIG. 14 is a perspective view of a pulse wave measuring apparatus according to the fifth embodiment of the present invention. In FIG. 14, the state of measurement where the array-type capacitive pressure pulse wave sensor is pressed against a wrist is shown. FIG. 15 is a schematic cross sectional view of the wrist and the pulse wave measuring apparatus in the state of measurement shown in FIG. 14.

As shown in FIG. 14, the pulse wave measuring apparatus 100 according to the present embodiment is for measuring the pressure pulse wave at the wrist of the subject. Pulse wave measuring apparatus 100 primarily includes a table 110 having a rest 112 on which the wrist and the forearm of the arm 20 of the subject are placed, a fastening belt 130 serving as the securing means for securing the wrist portion of arm 200 rested on the table 110, and a sensor unit 120 attached to fastening belt 130 that incorporates therein one of the array-type capacitive pressure pulse wave sensors 1A–1D of the first through fourth embodiments described above.

As shown in FIG. 14, in the state where the wrist is secured against the table 110, the artery 210 extends in the direction parallel to the extending direction of arm 200. When a cuff 124 serving as the pressing means incorporated in a casing 122 of sensor unit 120 is inflated in this state, the array-type capacitive pressure pulse wave sensor 126 approaches the wrist, and the sensing surface of the sensor 126 is pressed against the surface of the wrist. Here, array-type capacitive pressure pulse wave sensor 126 is placed such that the lower electrodes 10 provided at the sensing surface extend in the direction approximately orthogonal to the extending direction of artery 210.

At the time of measurement, artery 210 is sandwiched between a radius 220 and the sensing surface of array-type capacitive pressure pulse wave sensor 126 from the both sides, and deformed to an approximately flat form. At least one capacitive element 40 is located immediately above the flattened part of artery 210.

According to the pulse wave measuring apparatus with such a configuration, it is possible to measure the pressure pulse wave highly accurately and stably using a pressure sensor of capacitive type that can be produced inexpensively.

In the first through fourth embodiments, the array-type capacitive pressure pulse wave sensors each have lower and upper electrodes arranged in 2×5 or 3×5 rows and columns. The present invention however is not restricted thereto. Further, in each of the array-type capacitive pressure pulse wave sensors in the first through fourth embodiments, the lower and upper electrodes are formed of copper strips and the spacer member is formed of silicon rubber. Their materials however are not restricted thereto.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An array-type capacitive pressure pulse wave sensor for measuring a waveform indicating a change in arterial pressure by pressing a surface of a living body, comprising:

m rows (m is a natural number of more than 1) of first electrodes arranged in parallel with each other to extend substantially linearly in a direction approximately orthogonal to an extending direction of an artery at the time of measurement;

n columns (n is a natural number of more than 1) of second electrodes arranged in parallel with each other, at a prescribed distance from said m first electrodes, to extend in a direction crossing the extending direction of said m first electrodes; and m×n capacitive elements formed at intersections of said m first electrodes and said n second electrodes;

said m×n capacitive elements being arranged in a staggered manner when seen in two dimensions, wherein each of said n second electrodes has a bent portion provided at a part of said second electrode located between the neighboring two first electrodes and not overlapping either of said neighboring first electrodes, the bent portion being bent in a direction crossing the extending direction of the artery.

2. An array-type capacitive pressure pulse wave sensor for measuring a waveform indicating a change in arterial pressure by pressing a surface of a living body, comprising:

m rows (m is a natural number of more than 1) of first electrodes arranged in parallel with each other to extend substantially linearly in a direction approximately orthogonal to an extending direction of an artery at the time of measurement;

n columns (n is a natural number of more than 1) of second electrodes arranged in parallel with each other, at a prescribed distance from said m first electrodes, to extend in a direction crossing the extending direction of said m first electrodes; and m×n capacitive elements formed at intersections of said m first electrodes and said n second electrodes;

said m×n capacitive elements being arranged in a staggered manner when seen in two dimensions, wherein said n columns of second electrodes extend substantially linearly, and said m rows of first electrodes and said n columns of second electrodes cross each other not orthogonally when seen in two dimensions.

3. A pulse wave measuring apparatus, comprising:

a sensor unit having the array-type capacitive pressure pulse wave sensor according to any of claim 1 or 2;

securing means for securing said sensor unit with respect to the living body; and pressing means for pressing said array-type capacitive pressure pulse wave sensor against the living body.

* * * * *

UNITED STATES PATENT AND TRADEMARK OFFICE
CERTIFICATE OF CORRECTION

| | | |
|---|---|---|
| PATENT NO. | : 7,069,791 B2 | Page 1 of 1 |
| APPLICATION NO. | : 11/175447 | |
| DATED | : July 4, 2006 | |
| INVENTOR(S) | : Masao Hashimoto et al. | |

It is certified that error appears in the above-identified patent and that said Letters Patent is hereby corrected as shown below:

On the title page: under Foreign Application Priority Data:

Delete "2004-210359" and replace it with --2004-201359--

Signed and Sealed this

Fifth Day of December, 2006

JON W. DUDAS
*Director of the United States Patent and Trademark Office*